United States Patent [19]

Harrsen et al.

[11] Patent Number: 4,675,520

[45] Date of Patent: Jun. 23, 1987

[54] METHOD AND DEVICE FOR OPTICALLY COUNTING SMALL PARTICLES

[75] Inventors: Jan Harrsen, Ellerau; Franz Grosse-Scharmann; Bernd Gattermann, both of Hude, all of Fed. Rep. of Germany

[73] Assignee: Amazonenwerke H., Dreyer GmbH & Co. K.G., Hasbergen-Gaste, Fed. Rep. of Germany

[21] Appl. No.: 738,155

[22] Filed: May 24, 1985

[30] Foreign Application Priority Data

May 28, 1984 [DE] Fed. Rep. of Germany ....... 3419883

[51] Int. Cl.⁴ .................... G06M 7/00; A01C 7/00
[52] U.S. Cl. ................ 250/222.2; 250/221; 377/53
[58] Field of Search ............... 250/221, 222.1, 222.2, 250/560; 356/335, 386, 383–387; 377/53, 10, 11; 364/555

[56] References Cited

U.S. PATENT DOCUMENTS

| | | | |
|---|---|---|---|
| 4,183,013 | 1/1980 | Agrawala et al. | 377/10 |
| 4,203,029 | 5/1980 | Kitchener et al. | 377/10 |
| 4,371,253 | 2/1983 | Day et al. | 350/166 |
| 4,384,201 | 5/1983 | Carroll et al. | 250/221 |
| 4,490,801 | 12/1984 | Hagan et al. | 250/560 |
| 4,589,079 | 5/1986 | Peter | 250/222.2 |

Primary Examiner—David C. Nelms
Assistant Examiner—Charles F. Wieland
Attorney, Agent, or Firm—Sprung Horn Kramer & Woods

[57] ABSTRACT

A method and device for optically counting small particles, like grains of seed and fertilizer and other materials employed in agriculture. The particles to be counted travel past a test field, interrupting as they do so a beam of light between a light emitter and a light detector. To make it possible to detect even several particles in the test field at the same time and to make the counting generally more precise, individual points where the path of a beam of light is interrupted by particles passing through the grid are detected in sequential scanning cycles by beams of light that create an optical grid and are retained in the form of information describing one or more particles, information describing the particles and obtained in different scanning cycles are compared, and counting signals that correspond to the number of individual particles passing through are derived from the variations in the interrupting points determined during the comparison.

14 Claims, 7 Drawing Figures

METHOD AND DEVICE FOR OPTICALLY COUNTING SMALL PARTICLES

BACKGROUND OF THE INVENTION

The present invention relates to method of and a device for optically counting small particles, like grains of seed and fertilizer and other materials employed in agriculture, in which the particles to be counted travel past a test field, interrupting as they do so a beam of light between a light emitter and a light detector. The invention also relates to a device for carrying out the process and having a light emitter on one side of the test field and a light receiver on the other side.

A method of this type is known, for example, from German Patent 2 534 130. Small particles, specifically seed that is being sown, is sent through a light barrier inside a test field. The light barrier generates a pulse every time its beam is interrupted. However, although the number of pulses does equal the number of particles passing through the light barrier under the assumption that they pass through individually and in order, when several particles pass through the test field essentially simultaneously, as may happen when the supply of particles to the test field cannot be controlled precisely enough for exactly one particle to enter the test field at a time, errors can occur due to the light barrier emitting only one pulse in this case as well.

SUMMARY OF THE INVENTION

The object of the present invention is to improve a method and device of the types initially described to the extent that even several particles in the test field at the same time will be detected individually, and the counting will be generally more precise than in the known embodiment.

This object is attained in accordance with the invention in that individual points where the path of a beam of light is interrupted by particles passing through the grid are detected in sequential scanning cycles by beams of light that create an optical grid and are retained in the form of information describing one or more particles, in that information describing the particles and obtained in different scanning cycles are compared, and in that counting signals that correspond to the number of individual particles passing through are derived from the variations in the interrupting points determined during the comparison.

These characteristics ensure that the test field is handled differentially, that is, at separate points or areas. This makes it possible to determine whether the beam of light is interrupted or intact at these individually handled points. When it is determined that a beam of light specific to and illuminating a point or area being scanned at a particular instant has been interrupted, the resulting information will unambiguously indicate that a particle or part of a particle is interrupting the beam. The areas in which it is determined during an initial scanning cycle that the path of light is interrupted are accordingly retained in the form of particle-descriptive information and in a data memory for example. The separate areas or points are then scanned in a subsequent cycle and the resulting information compared with that obtained during the first cycle. This makes it possible to follow the passage of individual particles in time and space. It accordingly also becomes possible to detect several particles that are located at various points in the test field but at the same time.

Whereas the method in accordance with the invention can be employed either with a one-dimensional view, meaning that the beams of light proceed from only one side and generate thereby a linear grid, or even with a three-dimensional view, wherein the beams of light generate a cubical grid, it has turned out to be practical to view the test field from two sides, meaning that an optical, two-dimensional grid of intersecting light beams is employed. Such a two-dimensional grid makes it possible, in contrast to a one-dimensional view, to also detect any particles that pass through the test field behind an initial particle along the direction of viewing. It is then practical with respect to evaluating the particle-descriptive information for the light beams to intersect at an angle of 90°.

In another practical embodiment of the method the information from from different scanning cycles is always processed in parallel. This makes more rapid interpretation than in serial processing possible.

In another practical embodiment of the invention, only one particle is counted when information typical of only one particle is obtained in an initial cycle and two or more particles are detected in subsequent cycles and when the information obtained for the other particles is absent once the first particle has passed through, and information corresponding to the established number is retained when information indicating further particles is also present in the subsequent cycles once the first particle has passed through. This measure ensures that what are called phantom particles can be eliminated from the count. Phantom particles are particles that are not actually present but seem to be present as the result of overlapping of the shadows of individual particles. This measure makes the count even more precise.

To improve precision even more, the points obtained during different cycles are added to obtain a volumetric measure, the resulting volume of particles is compared with a minimum and with a maximum, and a counting signal is released only when the resulting volumetric measure is between these limits. This measure ensures that only particles within a prescribed tolerance range will be accepted. Particles with different dimensions will be excluded from the count and foreign particles will not lead to errors in counting. The limiting values can be obtained from the detected volumetric data of a particular number of particles.

The method in accordance with the invention can be carried out with a device of the type initially described in which the light receivers are discrete photocells that allow a separate indication, constituting several elementary light barriers inside the test field, with their output signals being supplied to a processor, in which they are processed cyclically. Since the individual elementary light barriers create a light grid in the test field, it can be determined whether or not a particle is present in each area inside the field.

One practical embodiment of the device has two opposite rows of light-emitting diodes (LED's) and of photodiodes positioned at a right angle in such a way that the beams leaving the rows of LED's intersect, creating an optical grid, with the processor including a multiplier circuit in which the information received in the form of logical signals from one row X is multiplied with that from the other row Y in such a way as to produce for each scanning cycle a matrix Z characterizing the aspect of the test field from each of the rows of photodiodes. In the matrix obtained by these means the points at which the individual particles are located will be represented where a logical 1 is entered instead of a logical 0 for example.

In another practical embodiment of the invention the processor includes a scanner that scans the rows of the Z matrix and notes the corresponding position for each change from 0 to 1 or from 1 to 0 in a data field. This makes it possible to establish the actual position of the left edge and of the right edge of a particle and hence of the particle itself.

When the processor also includes a comparator circuit in which the data from the rows can be interrelated, it can be established if or how a particle-describing data field that has been obtained changes over time. This allows information as to the number of particles to be obtained.

The photodiodes can be discrete photocells with associated systems of amplifiers or a CCD image-sensor element with its series output signals supplied to the processor through a series-to-parallel converter.

The rows of LED's and of photodiodes can each be accommodated in a rotating glass tube, with a mechanism that rotates the tube, and a scraper to clean each tube as it rotates.

Some preferred embodiments of the invention will now be described with reference to the attached drawings, wherein

DETAILED DESCRIPTION OF THE PREFERRED EMBODIMENTS

Figure 1:
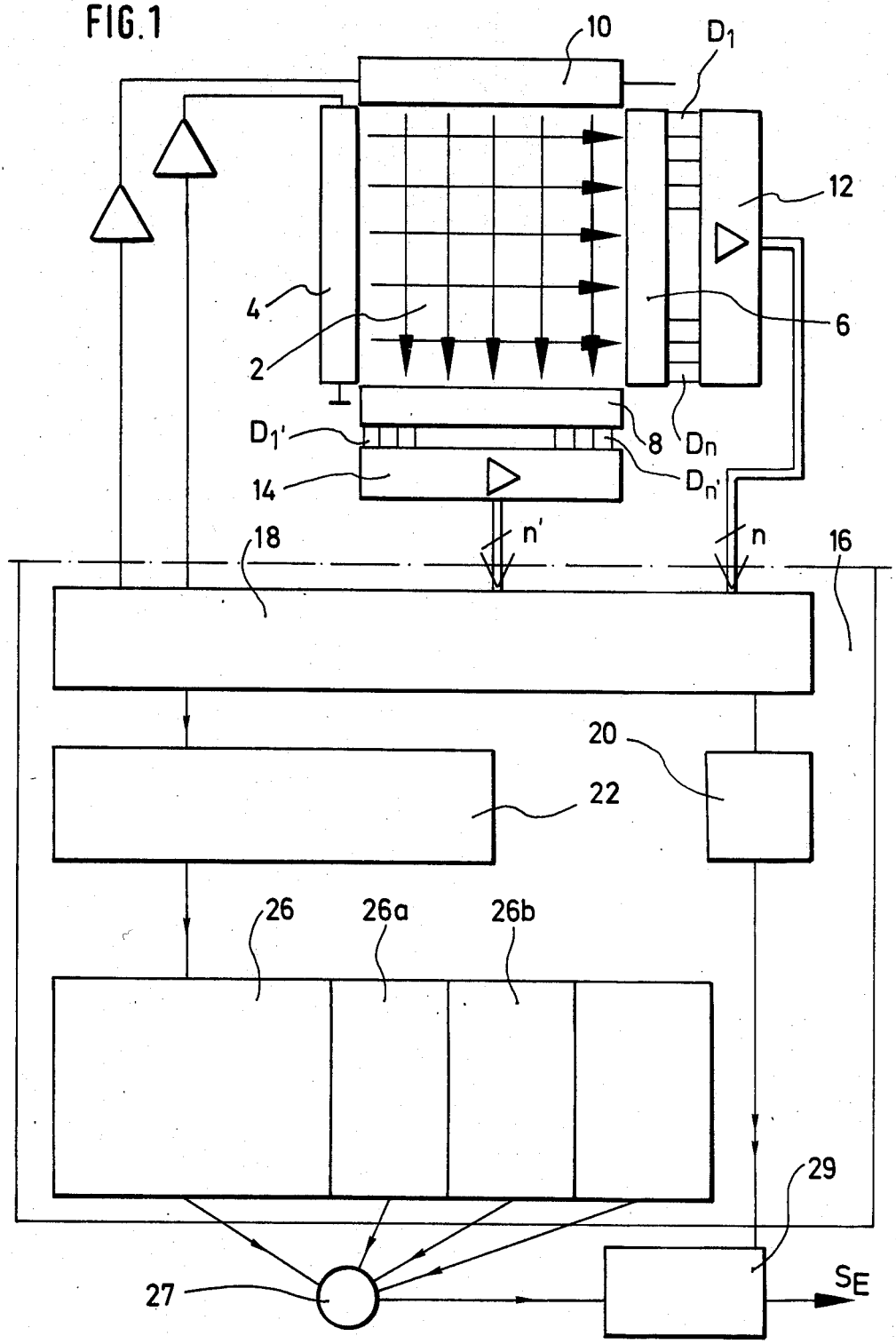
FIG. 1 is a block diagram of a device in accordance with the invention for carrying out the method in accordance with the invention.

FIG. 1 shows a test field 2 that individual particles like the grains of seed in a seed drill pass through in order to be counted. A row 4 of LED's and an opposite row 6 of photodiodes are positioned in a horizontal plane at the edges of test field 2. Another row 10 of LED s and another row 8 of photodiodes are positioned at an angle of 90° to the first rows. Since rows 6 and 8 of photodiodes consist of separate and adjacent photocells $D_1$-$D_n$ or $D_1'$-$D_{n'}$, test field 2 will be monitored by intersecting elementary light barriers that create a two-dimensional grid.

The selective signals obtained at the individual photocells $D_1$-$D_n$ or $D_1'$-$D_{n'}$, are amplified in associated amplifiers 12 or 14 and converted into logical signals.

Thus, a logical 0 is associated with a photodiode that is receiving a beam of light for example and a logical 1 with a photodiode that is not receiving a beam of light.

The resulting logical signals are processed in a processor 16, which will be described in detail later herein In processor 16 the row information is first detected in a scanner 18, with the individual states of the photocells $D_1$-$D_n$ or $D_1'$-$D_{n'}$, being determined for a particular time $t_n$. Data scanner 18 is connected to a timer 20 for this purpose.

Scanner 18 forwards the data to a buffer memory 22, which stores the signals that are present at a particular time in both row 6 of photodiodes (designated the Y row in what follows) and in row 8 of photodiodes (designated the X row in what follows). In other words, "snapshots" of the plane being crossed by the beams are taken, showing how the X and Y rows look at a particular time. These images are obtained at prescribed intervals and stored in buffer memory 22. From memory 22 the individual lines are forwarded to processor circuit 26, in which the information obtained in the various cycles is correlated, allowing the number of particles passing through the test field to be determined.

Figure 2A:
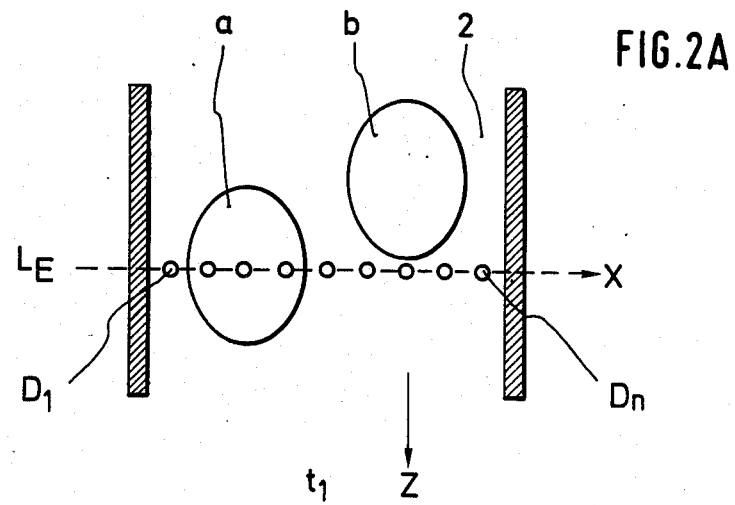
FIG. 2a is a longitudinal section through the test field showing two particles dropping through it essentially at the same time $t_1$.
Figure 2B:
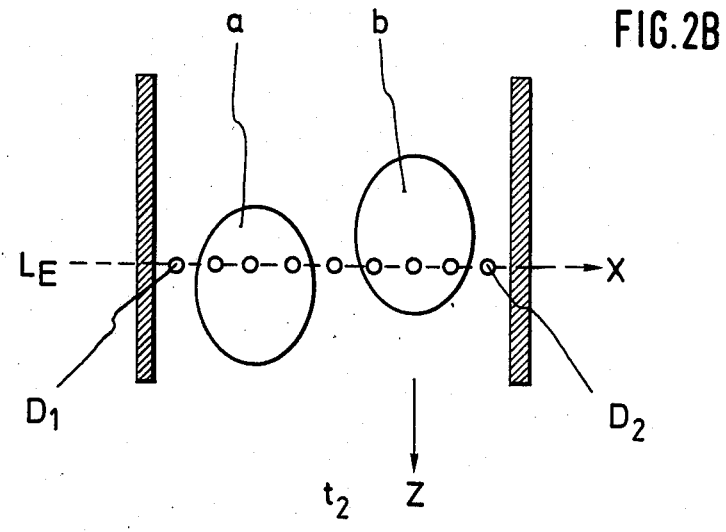
FIG. 2b is a longitudinal section through the test field showing two particles dropping through it essentially at the same time $t_2$, which is later than time $t_1$.

How this information as to the number of particles can be obtained will now be explained with reference to one example and to FIGS. 2a and 2b. Two particles a and b are falling through test field 2 in the direction indicated by arrow Z. An optical grid is generated in a plane $L_E$. FIG. 2a is a snapshot at time $t_1$ taken by the beams of light extending in the Y direction perpendicular to the plane of projection of the associated row of photodiodes, the individual photocells $D_1$-$D_n$ in which are represented by circles.

Thus, at time $t_1$ the row of photodiodes in question will generate the sequence of logical signals illustrated in Table 1 for the Y row at time $t_1$. A similar sequence of logical signals will be obtained in a similar way, not illustrated for the X row. At time $t_2$, illustrated in FIG. 2b, both particles will have fallen somewhat lower, so that (as illustrated in the figure again only for the Y row) the sequences listed in the table for the overall Y and X rows are obtained for time $t_2$.

TABLE 1

| Time | Y row | X row |
| --- | --- | --- |
| $t_1$ | 0111000000 | 0011100000 |
| $t_2$ | 0111011100 | 0011111100 |
| $t_3$ | 0000011100 | 0000011100 |
| $t_4$ | 0000000000 | 0000000000 |

The values obtained in this way for the X and Y rows are then multiplied together in the calculator to obtain a matrix Z for each row X, Y. The following matrices illustrate measurements for times $t_1$-$t_3$. It will be evident that the matrices represent an overview as seen from rows 6 or 8 of photodiodes at successive points in time.

| Matrix, time $t_1$ | | | | | | | | | | |
| --- | --- | --- | --- | --- | --- | --- | --- | --- | --- | --- |
| Y 0 | . | . | . | . | . | . | . | . | . | . |
| 1 | . | . | 1 | 1 | 1 | . | . | . | . | . |
| 2 | . | . | 1 | 1 | 1 | . | . | . | . | . |
| 3 | . | . | 1 | 1 | 1 | . | . | . | . | . |
| 4 | . | . | . | . | . | . | . | . | . | . |
| 5 | . | . | . | . | . | . | . | . | . | . |
| 6 | . | . | . | . | . | . | . | . | . | . |
| 7 | . | . | . | . | . | . | . | . | . | . |
| 8 | . | . | . | . | . | . | . | . | . | . |
| 9 | . | . | . | . | . | . | . | . | . | . |
| | 0 | 1 | 2 | 3 | 4 | 5 | 6 | 7 | 8 | 9 |
| | | | | | | | | | | X |

Matrix, time $t_2$

-continued

```
Y 0 .   .   .   .   .   .   .   .   .   .
  1 .   .   1   1   1   1   1   1   .   .
  2 .   .   1   1   1   1   1   1   .   .
  3 .   .   1   1   1   1   1   1   .   .
  4 .   .   .   .   .   .   .   .   .   .
  5 .   .   1   1   1   1   1   1   .   .
  6 .   .   1   1   1   1   1   1   .   .
  7 .   .   1   1   1   1   1   1   .   .
  8 .   .   .   .   .   .   .   .   .   .
  9 .   .   .   .   .   .   .   .   .   .
    0   1   2   3   4   5   6   7   8   9
                                          X
```

Matrix, time $t_3$

```
Y 0 .   .   .   .   .   .   .   .   .   .
  1 .   .   .   .   .   .   .   .   .   .
  2 .   .   .   .   .   .   .   .   .   .
  3 .   .   .   .   .   .   .   .   .   .
  4 .   .   .   .   .   .   .   .   .   .
  5 .   .   .   .   .   1   1   1   .   .
  6 .   .   .   .   .   1   1   1   .   .
  7 .   .   .   .   .   1   1   1   .   .
  8 .   .   .   .   .   .   .   .   .   .
  9 .   .   .   .   .   .   .   .   .   .
    0   1   2   3   4   5   6   7   8   9
                                          X
```

The rows of the Z matrix are then scanned. When there is an alteration from 0 to 1 that corresponds to the left edge of a particle, the actual position of the particle in a data field associated with the particle is noted. From that point on, all the 1 information up to an alteration from 1 to 0, corresponding to the left edge of a particle, is counted. Upon arrival at an alteration from 1 to 0 the limiting position of the particle is noted for comparison with the next row.

This process results in "particle-descriptive" information or data fields for each particle detected and providing a decision as to the dimensions and shape of the particle.

Comparison of the particle-descriptive information obtained for the individual rows now makes it possible to determine how the particles are moving through the test field. It will either be established upon comparison that no alterations are occurring or that there is an increase, a stabilization, or a decrease in the extent. The statement "one particle" can now be assigned to this established sequence.

Figure 3A:
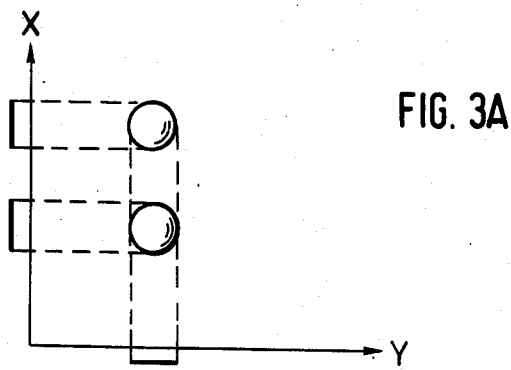
FIG. 3a is a diagram illustrating how two particles passing through the test field at the same time are detected.
Figure 3B:
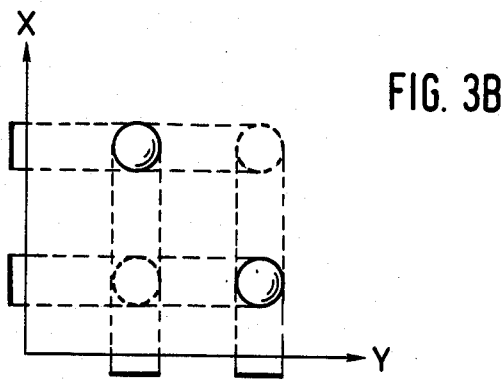
FIG. 3b is a diagram illustrating the problems that occur in a two-dimensional scanning system.

The two-dimensional system makes it possible to detect two particles that are subsequent in relation to one scanning direction and adjacent in relation to the other (FIG. 3a). When, of course, two particles are mutually displaced, phantom particles that are not actually present will be indicated as the result of the overlapping of the shadows of the actual particles in this system of interpretation.

To eliminate this problem and allow a more precise determination of the particles actually passing through the test field, it is first assumed in interpreting the results in the processor circuit that, when a group of two or more particles develops from a particle detected in the Z matrix, the cause is to be sought in a second particle. The phantom particles will accordingly disappear from the results when the end of the first particle is arrived at. In this case, then, only one particle will be counted.

If the phantom particles do not disappear from the resulting Z matrix, meaning in other words when not only one particle remains visible, it will be inferred that several particles must have entered the field at the same time. A signal corresponding to the number of detected particles will then be generated.

In addition to this supplementary test, which in carried out symbolically in an analysis block 26a in processor circuit 26, still other analyses can be carried out in further analyses blocks 26b etc. to obtain still further refinement of the results.

This potential for additional analyses is realized when, before the output signal representing one particle is generated, a volumetric measurement or particle volume measure obtained by addition of the line values in the matrix is taken and compared with a minimum and a maximum. Particles are then accepted only when they are in the intermediate range. The minimal and maximal limiting values can be selected from the volumetric data of a prescribed number of particles. This additional analysis can be employed to exclude foreign particles from the count.

Once these analyses or processing steps have been out in blocks 26, 26a, and 26b, the results are compiled at 27. The number of grains per unit of time is determined in circuit 29 and emitted in the form of a result signal $S_E$.

Figure 4:
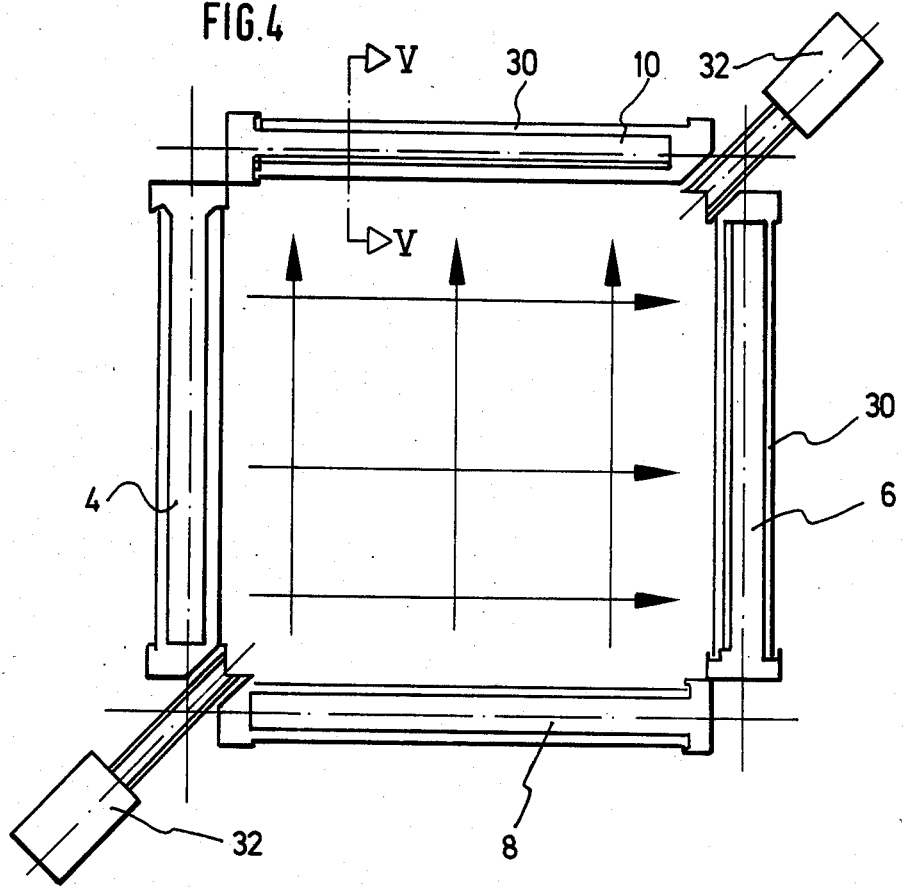
FIG. 4 illustrates how the LED's and photodiodes are mounted in such a way that they can be cleaned.
Figure 5:
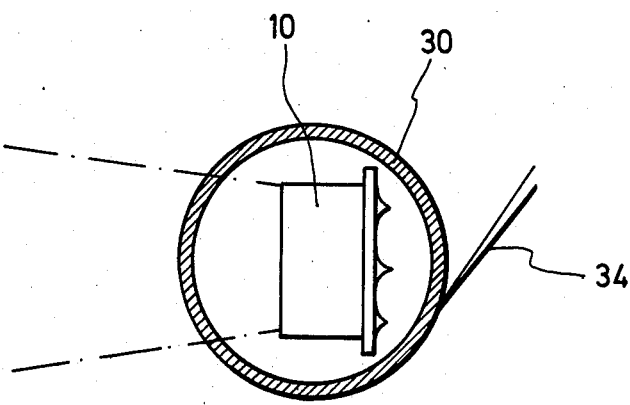
FIG. 5 is a section along the line V—V in FIG. 4.

To ensure even more that the results are not falsified by contamination of the optical elements the elements can or should be cleaned. One way of doing this is illustrated in FIGS. 4 and 5. The rows of LED's and of photodiodes are accommodated in a rotating glass case 30. There is a drive mechanism 32 at each diagonally opposite corner that rotates the glass tubes around the rows of LED's and of photodiodes in an appropriate way.

A scraper 34 in FIG. 5 sweeps the surface of the glass tubes and cleans them as they are driven around in a circle.

It will be appreciated that the instant specification and claims are set forth by way of illustration and not limitation, and that various modifications and changes may be made without departing from the spirit and scope of the present invention.

What is claimed is:

1. In a method of optically counting small particles, like grains of seed and fertilizer employed in agriculture, wherein particles to be counted travel past a test field, interrupting as they do so a beam of light between a light emitter and a light detector, the improvement comprising providing the test field with an optical grid having a plurality of beams of light, detecting individual points where the path of a beam of light is interrupted by free-falling particles passing through the grid in sequential scanning cycles, retaining the detected interruptions for each cycle in the form of information describing one or more particles, comparing information describing the particles and obtained in different scanning cycles and deriving counting signals that correspond to the number of individual particles passing through the optical grid from the variations in the interruptions of the points determined during the comparison.

2. The method as in claim 1, wherein the optical grid is two-dimensional and generated by intersecting beams of light.

3. The method as in claim 2, wherein the beams of light intersect at an angle of 90°.

4. The method as in claim 1, wherein the information from different scanning cycles is processed in parallel.

5. The method as in claim 1, wherein the step of deriving comprises producing a counting signal corresponding to only one particle when information typical of only one particle is obtained in an initial cycle and information typical of at least two particles is obtained in subsequent cycles and when information obtained for the at least other two particles is absent once said one particle has passed through the optical grid, and producing a counting signal corresponding to more than one particle when information typical of particles is also present in the subsequent cycles once said one particle has passed through the optical grid.

6. The method as in claim 1, wherein the points obtained during different cycles are added to obtain a volumetric measure, the resulting volume of particles is compared with a minimum and with a maximum, and a counting signal is produced only when the resulting volumetric measure is between the minimum and the maximum.

7. The method as in claim 6, wherein the minimum and maximum are obtained from the detected volumetric data of a particular number of particles.

8. A device for optically counting small particles, like grains of seed and fertilizer employed in agriculture, comprising a test field including means forming an optical grid having beams of light through which free-falling particles to be counted pass, comprising light emitters and light detectors, wherein the light detectors are discrete photocells that produce output signals to individually indicate when the associated light beam has been interrupted, and a processor receptive of the output signals from the photocells for processing the output signals cyclically comprising means for detecting individual photocell outputs where the path of a beam of light is interrupted by particles passing through the grid in sequential scanning cycles, means for retaining the detected interruptions for each cycle in the form of information describing one or more particles, means for comparing information describing the particles and obtained in different scanning cycles and means for deriving counting signals that correspond to the number of individual particles passing through the optical grid from the variations in the interruptions of the points determined during the comparison.

9. The device as in claim 8, wherein the optical grid has two opposite rows of light emitter comprising light-emitting diodes and of light detectors comprising photodiodes positioned at right angles in such a way that the beams leaving the rows of light-emitting diodes intersect, creating the optical grid, the deriving means comprises a multiplier circuit in which the information received in the form of logical signals from one row is multiplied with that from the other row in such a way as to produce for each scanning cycle a matrix characteristic of the test field from each of the rows of photodiodes.

10. The device as in claim 9, wherein the deriving means further includes a scanner that scans the rows of the matrix and notes the corresponding position for each change from 0 to 1 or from 1 to 0 in the matrix.

11. The device as in claim 10, wherein the comparing means includes a comparator circuit in which the data from the rows can be interrelated.

12. The device as in claim 11, wherein the photodiodes are discrete photocells with associated systems of amplifiers.

13. The device as in claim 11, wherein the photodiodes are a CCD image-sensor element with its series output signals supplied to the processor through a series-to-parallel converter.

14. The device as in claim 9, wherein optical grid comprises a glass tube accommodating the rows of light emitting diodes and photodiodes, means for rotating the tube, and a scraper to clean each tube as it rotates.

* * * * *